United States Patent
Schnitzler

(10) Patent No.: US 7,717,911 B2
(45) Date of Patent: May 18, 2010

(54) INSTRUMENT FOR PLASMA COAGULATION

(75) Inventor: Uwe Schnitzler, Tubingen (DE)

(73) Assignee: Erbe Elektromedizin GmbH, Tubingen (DE)

( * ) Notice: Subject to any disclaimer, the term of this patent is extended or adjusted under 35 U.S.C. 154(b) by 482 days.

(21) Appl. No.: 10/595,682

(22) PCT Filed: Oct. 29, 2004

(86) PCT No.: PCT/EP2004/012260

§ 371 (c)(1), (2), (4) Date: May 4, 2006

(87) PCT Pub. No.: WO2005/046495

PCT Pub. Date: May 26, 2005

(65) Prior Publication Data

US 2008/0243114 A1    Oct. 2, 2008

(30) Foreign Application Priority Data

Nov. 4, 2003   (DE) ................ 103 51 370

(51) Int. Cl.
   *A61B 18/14*   (2006.01)
(52) U.S. Cl. ........................ 606/40; 606/49
(58) Field of Classification Search ........ 606/37–40, 606/45, 49
   See application file for complete search history.

(56) References Cited

U.S. PATENT DOCUMENTS

| | | | |
|---|---|---|---|
| 5,320,621 A | 6/1994 | Gordon et al. | |
| 6,197,026 B1 * | 3/2001 | Farin et al. | 606/49 |
| 6,391,027 B1 * | 5/2002 | Farin et al. | 606/45 |
| 6,579,289 B2 * | 6/2003 | Schnitzler | 606/49 |
| 2001/0034519 A1 * | 10/2001 | Goble et al. | 606/41 |
| 2002/0016590 A1 | 2/2002 | Schnitzler | |
| 2002/0161362 A1 | 10/2002 | Penny et al. | |

FOREIGN PATENT DOCUMENTS

| | | |
|---|---|---|
| DE | 100 30 111 A1 | 1/2002 |
| EP | 0 740 926 A2 | 11/1996 |
| EP | 1 293 169 A1 | 3/2003 |
| EP | 1 293 170 A1 | 3/2003 |

* cited by examiner

*Primary Examiner*—Linda C Dvorak
*Assistant Examiner*—Benjamin Lee
(74) *Attorney, Agent, or Firm*—Dickstein Shapiro LLP

(57) ABSTRACT

For the coagulation of tissue by plasma, instruments are known that comprise a tubular probe body through which inert gas is conducted and an ignition electrode within the lumen in the region of an outlet of the probe body. A current conductor is provided to supply a coagulation current to the ignition electrode. The ignition electrode is fixed to the probe body substantially in the middle, by means of fixing devices. The present invention provides an instrument for plasma coagulation wherein a fixing device for the ignition electrode comprises a piece of sheet metal, a wafer or similar flat body, which is fixed by its longitudinal edges to the tube wall so that it extends substantially diametrically across the lumen, and to which the ignition electrode is attached.

10 Claims, 2 Drawing Sheets

INSTRUMENT FOR PLASMA COAGULATION

CROSS-REFERENCE TO RELATED APPLICATIONS

This application is a section 371 of International Application No. PCT/EP2004/012260, filed Oct. 29, 2004, which was published in the German language on May 26, 2005, under International Publication No. WO 2005/046495 A1 and the disclosure of which is incorporated herein by reference.

BACKGROUND OF THE INVENTION

The invention relates to an instrument for plasma coagulation.

Such an instrument is known for example from the document EP-1293170, and in the following is explained with reference to FIG. 3.

In FIG. 3 a probe for coagulation of tissue by means of plasma, specifically by means of argon (APC), is shown as a longitudinal section through the end section of the probe, which during an operation projects out of the opening of the working channel of an endoscope. Argon gas flows through the lumen 11 of a probe body 10 and emerges from an outlet 12 of the probe body 10.

Within the lumen 11 of the probe body 10 is an ignition electrode 20 that comprises, at its end opposite to a tip 21, a helical section 6 coiled in such a way that the outer circumference of the helix 6 is apposed firmly to a tube wall 13 of the probe body 10, or is fixedly attached thereto. The end of the helical section 6 opposite to the ignition electrode 20 is connected by way of a crimp tubule 7 to a current conductor 25 for supplying a coagulation current. The ignition electrode 20 is situated in the interior of a tubule 14 that is made of ceramic and likewise is firmly pressed into the tube wall 13. The arrangement here is such that the ignition electrode 20 with its tip 21 is set back by a prespecified amount from the outlet 12 of the tube body 10, or of the tubule 14 situated therein. Furthermore, the ignition electrode 20 occupies a precisely coaxial position within the tubule 14, so that symmetrical relationships are produced when the argon that flows past the ignition electrode 20 and its tip 21 and then emerges through the outlet 12 is ionized by the coagulation current and thus, in the known manner, produces a plasma that coagulates the tissue to be treated.

The known arrangement raises many problems, with regard in particular to manufacture but also to the operation of the instrument, in particular long-term operation.

First, it is difficult to provide the ignition electrode 20 with a helical section 6 having sufficiently precise construction that when it is pressed into the probe body 10, the ignition electrode 20 and in particular the tip 21 are positioned exactly in the middle, i.e. are coaxial with the tubule 14. Another problem arises in that the distance separating the tip 21 from the outlet 12 of the tubule 14 depends on the depth to which the helix 6 has been pressed in. Even placing the helix 6 in direct contact with the back end of the tubule 14 cannot alleviate this problem, because pressing too firmly would cause a change in position and/or angle of the ignition electrode 20.

The connection between the current conductor 25 and the electrode 20 by way of the crimp tubule 7 requires much effort to produce, in which respect it should always be kept in mind that the lumen 11 has a very small diameter, in the case of probes a diameter in the lower mm range or even below that.

Another problem with the known instrument resides in the fact that in particular the helical section 6 and its transition to the straight ignition electrode 20 cause, firstly, a constriction of the space through which the inert gas flows, and furthermore in the transition region between the helical section 6 and the interior of the tubule an asymmetry is present, which results in nonuniform gas-flow relationships within the tubule 14. All these asymmetries and constrictions interfere with the plasma generation and in particular result in poor reproducibility of instruments manufactured in series, with regard to their ignition behavior.

In a thermal respect, as well, the known state of the art raises problems. That is, the plasma causes heating and even burning away of the ignition electrode 20, so that the burning behavior, and in particular the ignition behavior of the instrument, changes while it is in use, which in turn makes it necessary to readjust the coagulation current (and/or the amplitude of the applied HF voltage).

BRIEF SUMMARY OF THE INVENTION

An object of the present invention is to develop an instrument of the kind cited above further in such a way that, while simplifying the construction and hence manufacturing procedure, an improved reproducibility of the ignition and burning behavior is provided.

This objective is achieved by the provision of an instrument for plasma coagulation (APC) wherein the electrode-fixing device comprises a metal sheet, a wafer or similar flat body, the longitudinal edges by means of which said flat body is attached to the tube wall so that the device extends substantially diametrically across the lumen, and the ignition electrode is attached to the fixing device.

This construction in accordance with the invention firstly facilitates fixing of the ignition electrode within the probe body, because there is no longer any need to coil a helical section. Furthermore, because the fixing device is flat, the inert gas that flows by can cool it as well as the ignition electrode attached to it. The fact that the flat body is in contact at its two edges with the tube wall ensures a symmetrical construction, in particular at the transition between the flat body, i.e. the section that holds the ignition electrode, and the ignition electrode itself, which in turn produces symmetrical flow relationships and in particular causes no substantial alterations of the lumen of the probe body. It is very simple to press the flat body into the lumen of the probe body, because it is stiff in itself and is not—as a helical structure would be—placed under tension while being inserted, in which case these tensions would have to be compensated during subsequent use, which could cause changes of position.

The current conductor in one embodiment of the invention is integrally connected to the ignition electrode. In this case a tungsten wire can be used, which extends continuously from the ignition electrode over the fixing wafer or other flat fixing device and on to the plug by way of which the current conductor is connected to the electrosurgical instrument.

Alternatively, the current conductor is connected to the ignition electrode by way of the flat body of the fixing device, so that said device, i.e. the means by which the ignition electrode is held within the probe body, replaces the crimp tubule that is necessary in the known arrangement.

The ignition electrode and/or the current conductor are preferably welded to the flat body, i.e. are fixed by a means that is especially secure and simple to carry out. Particularly suitable for this purpose is resistance welding by way of weld points.

In the region of the outlet a tubule made of ceramic or a similar material that is resistant to high temperatures (as is known per se) can be inserted into the lumen, in which case the flat body is disposed at an end of the tubule facing away from the outlet. This embodiment achieves an increased stability of the arrangement. Preferably in this embodiment an abutment is provided between the flat body, i.e. an abutment formed by sections of its front end, and the tubule. This simple measure ensures a precise and unequivocally reproducible geometric alignment between the holder of the ignition electrode (i.e., the flat body) and the ceramic tubule that defines the outlet.

The flat body preferably comprises a concave cutout at its front edge, which faces the outlet. As a result, on one hand a sufficiently large connecting surface between the flat body and the tube wall is ensured, while on the other hand the lumen is kept free of constricting material over a longer section of the ignition electrode. This is very advantageous particularly when a ceramic tubule is used, against which the flat body abuts. In this case the cutout is situated ahead of the ceramic tubule, with regard to the flow direction of the inert gas, so that especially interference-free and symmetrical flow conditions within the tubule are ensured.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

In the following description, the same reference numerals are used for identical parts or parts with identical actions; in particular, those parts that have already been explained above in relation to FIG. 3 are not specifically explained again.

DETAILED DESCRIPTION OF THE INVENTION

Figure 1:
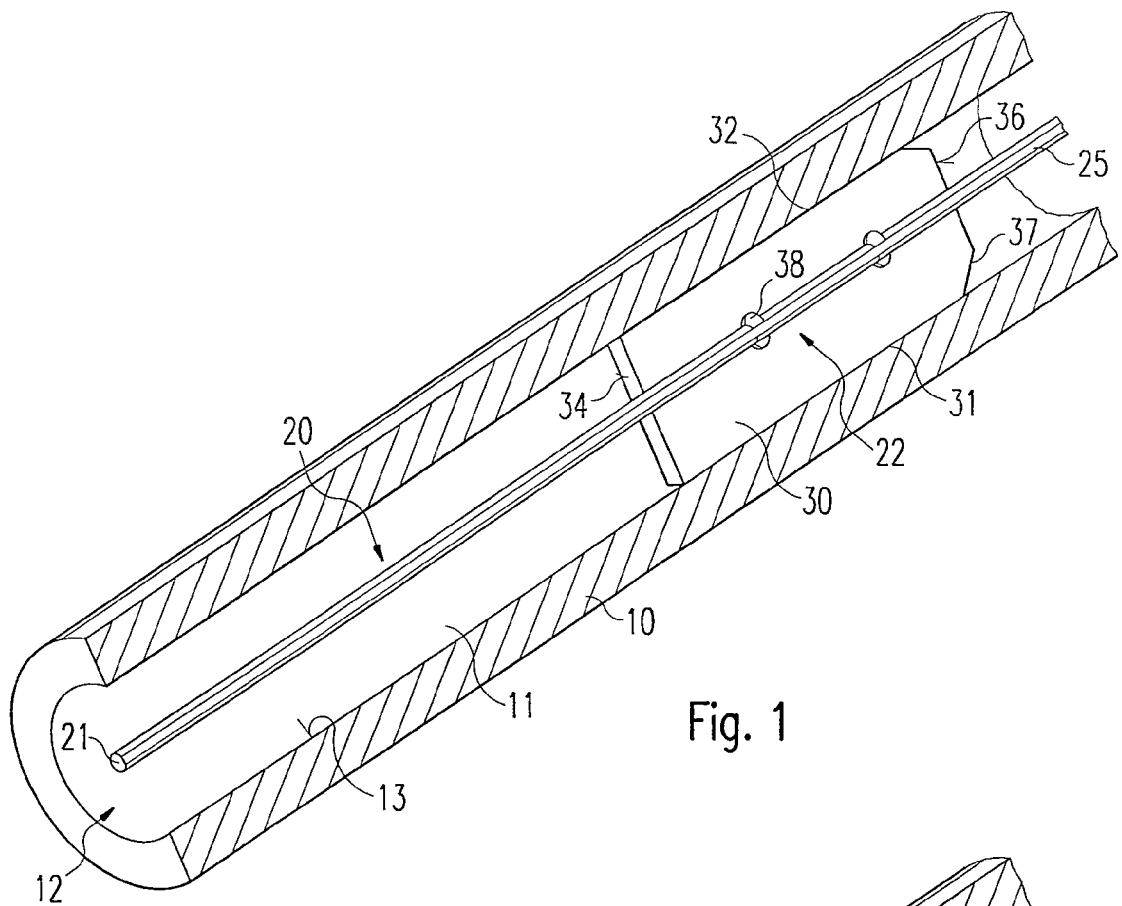
FIG. 1 shows a first preferred embodiment of the invention.

As is evident in FIG. 1, for fixing the ignition electrode 20 within a fixation region 22 there is provided a flat body 30 with longitudinal edges 31 and 32, which is pressed into the lumen 11 of the probe body 10 from its outlet 12 in such a way that these edges 31, 32 and hence the entire flat body 30 are in firm contact with the tube wall 13 of the probe body 10. To facilitate the pressing-in procedure, the flat body 30 comprises chamfers 37 at its back edge 36, i.e. the end opposite the outlet 12.

Fixation of the ignition electrode 20, which here is integrated with the current conductor 25 as a (tungsten) wire, to the flat body 30 is accomplished by means of weld points 38, which are preferably produced by point-wise resistance welding.

With the arrangement shown here it is readily conceivable that an exact, concentric arrangement of the ignition electrode 20 and in particular its tip 21 can very easily be achieved in that the flat body 30, preferably made of a sheet of steel or tungsten, is precisely manufactured and the ignition electrode 20 together with the current conductor 25 is attached by point welding precisely in the middle of the flat body. The concentric orientation of the flat body 30 within the lumen 11 occurs, so to speak, by itself on account of the precisely symmetrical construction of the lumen 11, i.e. the tube wall 13.

Figure 2:
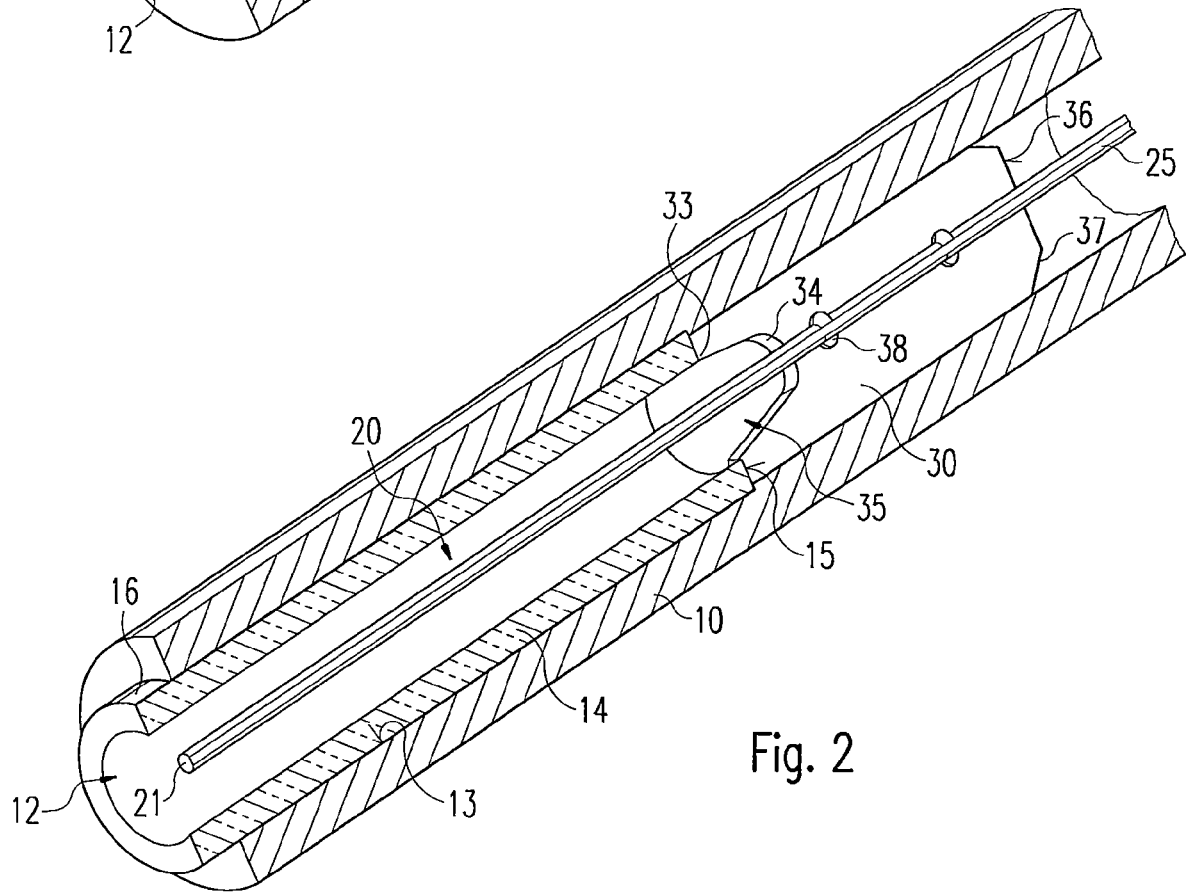
FIG. 2 shows a second preferred embodiment of the invention.
Figure 3:
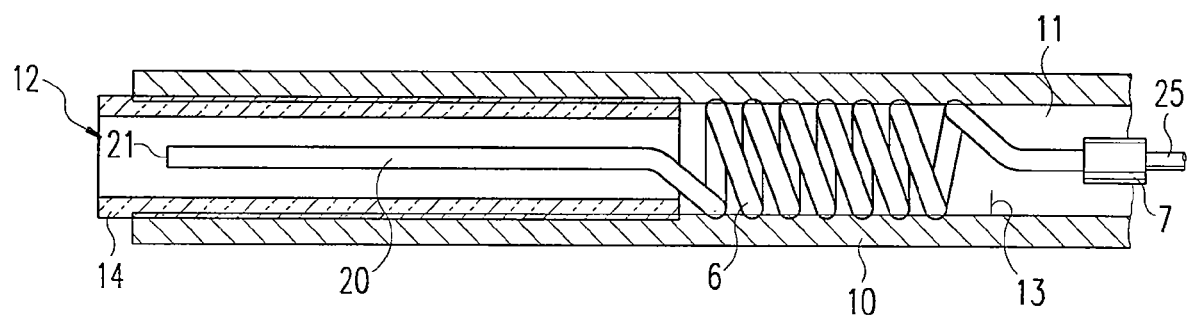
FIG. 3 shows an instrument according to the state of the art.

The embodiment according to FIG. 2 differs from that shown in FIG. 1 in that in the region of the end of the probe body (as is known per se) a ceramic tubule 14 is inserted. The flat body 30 comprises at its front edge 34, which faces the opening 12, a cutout section 35 which merges with abutments 33 next to the two longitudinal edges 31, 32. The abutments 33 are dimensioned such that they correspond substantially to the thickness of the tubule 14. This construction ensures on one hand exact and faultlessly reproducible geometric relationships between the flat body 30, together with the ignition electrode 20 attached thereto, and the tubule 14, which defines the outlet 12. The distance separating the tip 21 of the ignition electrode 20 from the outlet 12 does not depend on the process of fixing the ignition electrode within the probe body 10; it depends entirely on the precision of manufacturing the flat body 30 and fixing the ignition electrode 20 thereto, which can be ensured by using appropriate tools. Insofar, therefore, the contact between the abutment 33 of the flat body 30 and the back edge 15 of the tubule 14 constitutes an essential adjustment criterion.

In addition to the advantages of the flat body 30 described above, in particular with reference to cooling of the ignition electrode 20 (which achieves a better burning-away behavior), the cutout 35 ensures that the interior of the tubule 14 remains free even in its initial (with respect to the direction of gas flow) regions.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An instrument for plasma coagulation comprising: a tubular probe body with a tube wall defining a lumen through which an inert gas is conducted through the probe body; an ignition electrode located within the lumen in the region of an outlet defined by said probe body; a current conductor adapted to supply a coagulation current to said ignition electrode; a tubule made of a high-temperature-resistant material; and a fixing device fixing said ignition electrode in a predetermined position within said probe body, and comprising a flat body with longitudinal edges by means of which said flat body is attached to said tube wall such that said flat body extends diametrically across an entire width of said lumen, and to which the ignition electrode is attached such that the ignition electrode extends further into the lumen in a direction of said outlet than the flat body of the fixing device, wherein said tubule is inserted into said lumen in the region of said outlet, and said flat body is disposed at an end of the tubule that faces away from said outlet.

2. The instrument according to claim 1, wherein said current conductor is integrally connected to said ignition electrode.

3. The instrument according to claim 1, wherein said current conductor is connected to the ignition electrode by means of said flat body.

4. The instrument according to claim 1, wherein at least one of said ignition electrode and said current conductor is welded to said flat body.

5. The instrument according to claim 4, wherein said welded attachment is formed by point-wise resistance welding.

6. The instrument according to claim 1, wherein said flat body comprises a flat edge and abuts said tubule by means of sections of said flat edge.

7. The instrument according to claim 1, wherein said flat body comprises a flat edge that defines a concave cutout which faces toward said outlet.

8. The instrument according to claim 1, wherein said longitudinal edges of said flat body extend further into said lumen in a direction of said outlet than a center of an outlet-facing edge of said flat body.

9. An instrument for plasma coagulation comprising:
a tubular probe body with a tube wall defining a lumen through which an inert gas is conducted through the probe body;
an ignition electrode located within the lumen in the region of an outlet defined by said probe body;
a current conductor adapted to supply a coagulation current to said ignition electrode; and
a fixing device fixing said ignition electrode in a predetermined position within said probe body, and comprising a flat body with longitudinal edges by means of which said flat body is attached to said tube wall such that said flat body extends diametrically across an entire width of said lumen, and to which the ignition electrode is attached such that the ignition electrode extends further into the lumen in a direction of said outlet than the flat body of the fixing device.

10. The instrument according to claim 9, wherein said longitudinal edges of said flat body extend further into said lumen in a direction of said outlet than a center of an outlet-facing edge of said flat body.

* * * * *